United States Patent [19]

Hansen

[11] Patent Number: 4,687,797

[45] Date of Patent: Aug. 18, 1987

[54] HALO PHTHALIMIDES OF PHENOLIC-SUBSTITUTED HYDRAZIDES

[75] Inventor: Ralph H. Hansen, Lincoln, Mass.

[73] Assignee: Canusa Coating Systems Limited, Rexdale, Canada

[21] Appl. No.: 901,974

[22] Filed: Sep. 2, 1986

Related U.S. Application Data

[63] Continuation of Ser. No. 715,011, Mar. 22, 1985, abandoned, which is a continuation of Ser. No. 536,341, Sep. 27, 1983, Pat. No. 4,520,146.

[51] Int. Cl.$^4$ .................. C07D 209/48; C08K 5/34
[52] U.S. Cl. ........................... 524/94; 548/475
[58] Field of Search ................. 524/94; 548/475

[56] References Cited

U.S. PATENT DOCUMENTS

| | | | |
|---|---|---|---|
| 3,734,925 | 5/1973 | Minieri | 548/375 |
| 3,873,567 | 3/1975 | Cyba | 524/94 |
| 3,887,518 | 6/1975 | Rosenberger et al. | 524/94 |
| 3,906,002 | 9/1975 | Stephen | 524/94 |
| 3,933,736 | 1/1976 | Yoshikawa et al. | 524/94 |
| 3,959,216 | 5/1976 | Richter et al. | 524/94 |
| 3,978,156 | 8/1976 | Parker et al. | 524/94 |
| 4,001,065 | 1/1977 | Dexter | 524/194 |
| 4,001,179 | 1/1977 | Richter et al. | 524/94 |
| 4,015,058 | 3/1977 | Schober | 526/57 |
| 4,045,404 | 8/1977 | Stephen | 524/57 |
| 4,116,930 | 9/1978 | Dexter et al. | 524/89 |

FOREIGN PATENT DOCUMENTS 2648970 5/1978 Fed. Rep. of Germany .
1514500 6/1978 United Kingdom .

*Primary Examiner*—Veronica P. Hoke
*Attorney, Agent, or Firm*—Donald Brown

[57] ABSTRACT

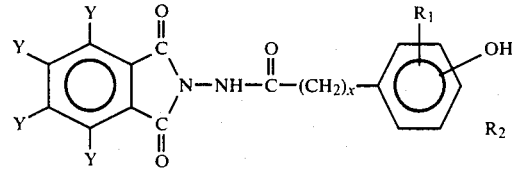

where X is 1, 2 or 3; Y is Cl or Br; $R_1$ is tert-butyl (t-butyl) and $R_2$ is H or lower alkyl of 1 to 4 carbons. The preferred group of compounds is where OH is at the 4 position, $R_1$ is at the 3 position and $R_2$ is at the 5 position of the phenyl ring. The most preferred compound is where X is 2, $R_1$ and $R_2$ are both t-butyl at the 3 and 5 positions of the phenyl ring and OH is at the 4 position of the phenyl ring and Y is Br. The compounds are useful as antioxidants and flame retardants.

6 Claims, 7 Drawing Figures

HALO PHTHALIMIDES OF PHENOLIC-SUBSTITUTED HYDRAZIDES

This application is a continuation of application Ser. No. 715,011, filed Mar. 22, 1985, abandoned, which is a continuation of Ser. No. 536,314 filed Sept. 27, 1983, now U.S. Pat. No. 4,520,146.

BRIEF STATEMENT OF THE INVENTION

This invention is directed to compounds of the formula (I)

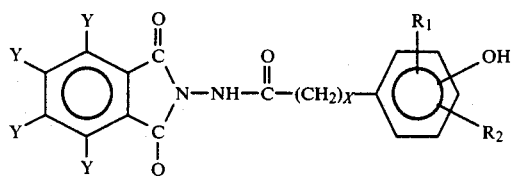

where X is 0, 1, or 2; Y is Cl or Br; $R_1$ is tert-butyl (t-butyl); and $R_2$ is H or lower alkyl of 1 to 4 carbons, e.g., methyl, ethyl, propyl or butyl (e.g., t-butyl).

The preferred group of compounds is where OH is at the 4 position, $R_1$ is at the 3 position and $R_2$ is at the 5 position of the phenyl ring. The most preferred compound is where X is 2, $R_1$ and $R_2$ are both t-butyl at the 3 and 5 positions of the phenyl ring and OH is at the 4 position of the phenyl ring and each Y is Br.

The compounds of formula I are useful as antioxidants and flame retardants in polymers and in articles of manufacture.

The compounds of formula I are substantially non-blooming in comparison to most other antioxidants.

The present invention is useful in polymers used for electrical insulation, in heat shrinkable tubing and other parts, e.g., end caps made of polyethylene and used for electrical purposes, as well as in other plastic (polymer) parts used as utensils or as parts of the tubs of washing machines to prevent them from becoming brittle due to loss of antioxidant (because of soapy water causing the antioxidants commonly used to leach out of the plastic).

The compounds of formula (I) are particularly useful in heat recoverable (heat shrinkable) articles of manufacture such as tubing, end caps, boots and other hollow articles to which heat is applied to cause shrinkage because the lack of blooming permits coating with adhesives which may contain metal particles.

Polymers in which the compounds of formula (I) are useful in this invention include all thermoplastics and thermohardening (thermosetting) plastics in which antioxidants are employed. Suitable plastics may include polyolefins such as polyethylene (high and low density), polypropylene, polybutylene, substituted polyolefins such as halogenated olefin polymers and copolymers of same and silane grafted polyethylenes, e.g., grafted using a silane such as vinyl trimethoxy silane as the grafting agent. (See U.S. Pat. No. 3,086,242.)

The compounds of formula (I) would also be useful with any polymer whose useful properties are adversely affected by oxidative degradation such as esters, amides (e.g. nylon), phenolics, acrylics, rubber, urethanes, vinyls, styrenes (e.g. ABS), and others used inthe plastics industry. See the Text PLASTICS IN THE MODERN WORLD by E. G. Couzens and V. E. Yarsly © 1968, published by Pelican Books, Inc., Maryland U.S.A., for other polymers used in industry and useful in this invention.

Prior art patents showing heat recoverable plastics and articles include U.S. Pat. Nos. 4,048,129, 4,016,356, 3,981,546 and 3,959,052. It should be understood that heat recoverable articles are meant to include those that are treated by irradiation or chemically treated to produce such articles.

Compounds of this invention may be combined with other antioxidants useful in a polymer which include:

| ANTIOXIDANTS | |
|---|---|
| Commercial Name | Chemical Name |
| Irganox 1010 | tetrakis[methylene-3(3',5'-di-tert-butyl-4'-hydroxyphenyl)propionate]methane |
| Santonox R | 4,4'-thiobis(3-methyl-6-tert-butyl-phenol) |
| Irganox 1024 | N,N'—bis(3,5-di-tert-butyl-4-hydroxy-hydrocinnamoyl)hydrazine |
| Cyanox 1729 | Bis(4-tert-butyl-3 hydroxy-2,6-dimethyl benzyl) dithiolterephthalate |
| Ethyl 330 | 1,3,5,Trimethyl-2,4,6-tris[3,5-di-tert-butyl- 4 hydroxy benzyl]-benzene |
| Agerite White | di-B—naphthyl-p-phenylene-diamine |
| Irganox 1035 | thiodiethylene bis(3,5-di-tert-butyl-4-hydroxy) hydrocinnamate |

Other suitable commercial antioxidants include Good-Rite 3114, Plastanox 2246, Naugard 449, Naugard XL-1, Irganox 1093, Irganox 1076, Topanol CA, and Irganox 565. Other antioxidants in the art may be found in the text ANTIOXIDANTS, RECENT DEVELOPMENTS, CHEMICAL TECHNOLOGY REVIEW NO. 127, by M William Ronney, Noyes Data Corporation © 1979, Library of Congress, Catalog No. 79-84425.

In using the comound of formula (I) in a polymer the concentration used should preferably be between 0.05 to 10% of the weight of the polymer when used as an antioxidant and at concentrations as high as 150% (generally 50 to 100%) of the weight of the polymer for fire resistant compositions.

In FIGS. 1 to 7 there are shown various forms of the invention. FIGS. 1 to 5 illustrate hollow articles as does FIG. 7.

FIGS. 1, 2 and 3 illustrate a tube 20 formed of material such as vinyl trimethoxysilane grafted polyethylene and containing a compound of formula (I).

The tube is formed by conventional technology to be heat shrinkable e.g., see U.S. Pat. Nos. 3,086,242 and 3,303,243. See U.K. Patent Application No. 1601063 published Oct. 21, 1981 for an illustration of chemically produced heat shrinkable material. Conventional crosslinked silane grafted polyethylene is shown in U.S. Pat. No. 3086,242. The material of U.S. Pat. No. 3,086,242 will be modified by the incorporation of the comound of formula (I) as disclosed herein.

The tube 20 is shrunk as shown in FIG. 3 over electrical cable 21 to provide an insulative protective cover which will protect against moisture and other deleterious substances.

FIGS. 4 and 5 illustrate a heat recoverable end cap 25 (a closed at one end hollow article) with FIG. 5 showing the end cap 25 shrunk over a pair of o-wires 26 and 27. The end cap 25 is made by using the polymer material of the invention in a manner well known in the art.

FIGS. 6 and 7 show a sheet 30 of material of the invention rolled over upon itself as in FIG. 7 to form a tube. The sheet may be heat recoverable or not depending upon the desires of the end user. A heat recoverable sheet may be made by methods known in the art.

Figure 1:
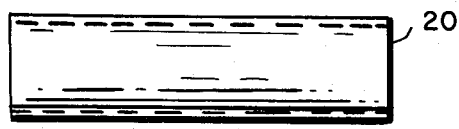
FIG. 1 is a side view of a tube.
Figure 2:
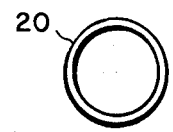
FIG. 2 is an end view of a tube.
Figure 3:
FIG. 3 is a sectional view of the tube of FIGS. 1 and 2 shrunk over wire or cable.
Figure 4:
FIG. 4 is a sectional view of an end cap.
Figure 6:
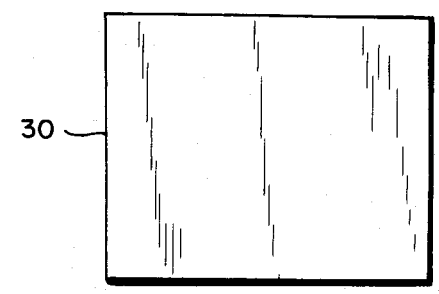
FIG. 6 is a top view of a sheet of polymer material of the invention.
Figure 5:
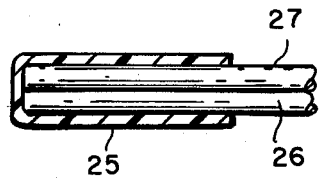
FIG. 5 is a sectional view of the end cap of FIG. 4 shrunk over a pair of wires.
Figure 7:
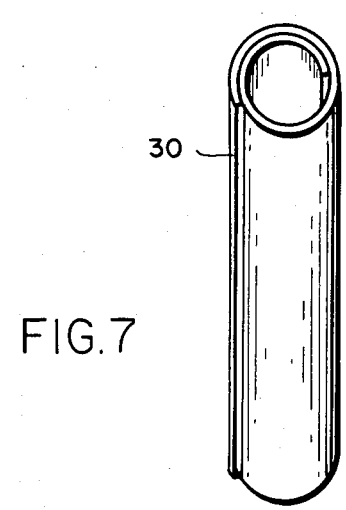
FIG. 7 is a perspective view of the sheet of FIG. 6 rolled up upon itself to form a tube.

The following examples are illustrative of the practice of the invention and are not intended for purposes of limitation. All parts are by weight and all temperatures are in centigrade.

EXAMPLE 1

Preparation of the preferred compound of formula (I) where each Y is Br and each R is t-butyl at the 3- and 5-position and OH is at the 4-position and X=2

The preferred compound of formula (I) is prepared in two steps as follows:

To 1500 ml. of methyl alcohol is added 642 grams of thiodiethylene bis(3,5-di-tert-butyl-4-hydroxy)hydrocinnamate. The mixture is sitrred and heated to about 55° C. to effect solution. At this point 80 grams of 95% hydrazine (20% excess) is added and heating is continued for three hours. The mixture is cooled and the crystals which separate are filtered and dried. A total of 210 grams of (3,5-di-tert-butyl-4-hydroxy)hydrocinnamic acid hydrazide is obtained (72% yeield). This material has a melting point of 158° C. (Perkin-Elmer DSC-2 calorimeter at a heating rate of 10° C. per minute). The yield may be increased by re-using the mother liquor in place of fresh methanol, by concentrating the mother liquor, or by diluting the mother liquor with a poor solvent for the hydrazide (such as water).

The dried hydrocinnamic acid hydrazide is used without further purification. A mixture of 29.2 grams of the hydrazide and 46 grams of powdered tetrabromophthalic anhydride is added to 1000 ml. of water and stirred at room temperature for about two hours. The temperature is then gradually increased to 100° C. over a 2-hour period, with stirring. The product obtained is filtered while hot, washed with hot water and dried. The yield was 64 grams (85%) of the compound having a small endotherm at 286° C. and a main melting point at 303° C. (Perkin-Elmer DSC-2 calorimeter at a heating rate of 10° C. per minute and with an oxygen atmosphere, which demonstrates the resistance of the compound to oxidation by atmospheric oxidation). It is substantially white and is insoluble in boiling water.

EXAMPLE 2

Using the compound of formula (I) prepared in Example 1, a number of compositions are prepared by mixing the proportions of ingredients (percent by weight shown) into a polymer comprising 9% vinyl acetate—91% ethylene copolymer (commerically known as U.S. Industrial Chemicals UE 635) or low density polyethylene, on a heated, two-roll mill, molding into a sheet approximately 75 mils thick as shown below:

(i) 3 parts by weight of the compound of formula (I) and 100 parts by weight of the polymer (VE635); and (ii) 10 parts by weight of the compound of formula (I) and 90 parts by weight of the polymer (polyethylene) (NA 254); and (iii) 0.047 part by weight of the compound of formula (I) and 100 parts by weight of a polyethylene polymer (commercially known as U.S. Industrial Chemicals NA 254).

I claim:

1. The compound of the formula I

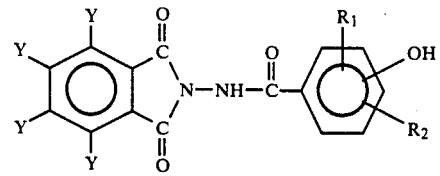

where Y is Cl or Br; $R_1$ is tert-butyl and $R_2$ is H or lower alkyl of 1 to 4 carbons.

2. The compound of the formula I

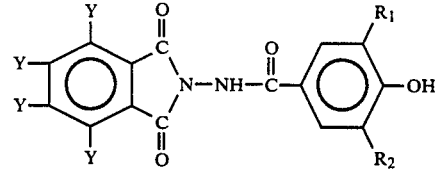

where Y is Cl or Br; $R_1$ is tert-butyl; $R_2$ is H or is lower alkyl of 1 to 4 carbons.

3. A composition comprising a polymer and the compound of claim 1 in an amount sufficient to impart flame retardant and antioxidant properties.

4. A composition comprising a polyolefin polymer and the compound of claim 2 in an amount sufficient to impart flame retardant and antioxidant properties.

5. A heat shrinkable article comprising a polymer and the compound of claim 1 in an amount sufficient to impart flame retardant and antioxidant properties.

6. A heat shrinkable article comprising polyethylene crosslinked with vinyl trimethoxysilane and the compound of claim 2 in an amount sufficient to impart flame retardant and antioxidant properties.

* * * * *